United States Patent [19]
Schlapfer et al.

[11] Patent Number: 5,498,264
[45] Date of Patent: Mar. 12, 1996

[54] CLAMP CONNECTION FOR CONNECTING TWO CONSTRUCTION COMPONENTS FOR A SETTING DEVICE, PARTICULARLY AN OSTEOSYNTHETIC SETTING DEVICE

[75] Inventors: Johannes F. Schlapfer, Glarus; Martin Hess, Holstein; Roland Woreth, Arlesheim; Peter Tanner, Bubendorf; Hans Weigum, Niederdorf, all of Switzerland

[73] Assignee: Synthes (U.S.A.), Paoli, Pa.

[21] Appl. No.: 363,588

[22] Filed: Dec. 23, 1994

Related U.S. Application Data

[63] Continuation of Ser. No. 915,606, Jul. 21, 1992, abandoned.

[51] Int. Cl.⁶ .................................................. A61B 17/56
[52] U.S. Cl. .................. 606/72; 606/73; 606/61; 439/807; 403/261; 403/400
[58] Field of Search .................. 439/801, 807, 439/781; 403/261, 247, 256, 400; 606/60, 61, 72, 73

[56] References Cited

U.S. PATENT DOCUMENTS

| | | | |
|---|---|---|---|
| 231,637 | 8/1880 | Wilcox | 403/400 |
| 566,709 | 8/1886 | Bryan | 403/256 |
| 1,950,635 | 6/1930 | Steinmayer | 403/400 |
| 2,831,717 | 4/1968 | Mayer . | |
| 3,677,584 | 7/1972 | Short . | |
| 4,653,481 | 3/1987 | Howland | 606/61 |
| 5,000,705 | 3/1991 | Kinka | 439/807 |
| 5,030,220 | 7/1991 | Howland | 606/61 |
| 5,176,680 | 1/1993 | Vignaud | 606/61 |
| 5,222,954 | 6/1993 | Baker | 606/61 |

FOREIGN PATENT DOCUMENTS

| | | | |
|---|---|---|---|
| 67485 | 5/1940 | Czechoslovakia | 439/807 |
| 764675 | 11/1933 | France | 439/807 |
| 1261347 | 4/1961 | France | 403/400 |
| 699401 | 11/1940 | Germany | 439/807 |
| 1045181 | 11/1958 | Germany . | |
| 9101321 | 4/1991 | Germany . | |
| 1678 | of 1915 | United Kingdom | 403/400 |
| 8801152 | 2/1988 | United Kingdom . | |
| 9116020 | 10/1991 | WIPO | 606/61 |

*Primary Examiner*—Robert A. Hafer
*Assistant Examiner*—David J. Kenealy
*Attorney, Agent, or Firm*—Fish & Richardson

[57] ABSTRACT

A clamp connection serves to connect two construction components, in particular for an osteo-synthetic fixation device in a structure in which the construction components are off-set from the force axis of the loading force that retains them.

13 Claims, 3 Drawing Sheets

CLAMP CONNECTION FOR CONNECTING TWO CONSTRUCTION COMPONENTS FOR A SETTING DEVICE, PARTICULARLY AN OSTEOSYNTHETIC SETTING DEVICE

This is a continuation of application Ser. No. 07/915,606 filed on Jul. 21, 1992 abandoned.

FIELD OF THE INVENTION

This invention relates to a clamp for joining two longitudinal components to one another, particularly for use in osteosynthesis.

BACKGROUND OF THE INVENTION

In a prior clamp according to DE-GM 91 01 321, there are two approximately equal clamp components and a pressure disc positioned between them, the whole assembly being penetrated by a centrally positioned threaded screw of a loading device. The loading device rests on the top clamp component, and is screwed into the bottom clamp component. The clamp components have two semi-cylindrical recesses that serve to hold rod shaped construction components. With this clamp two construction components can be permanently connected. Thus, for example, a carbon filament rod and a Schanz screw, are each inserted between a clamp component and the pressure disc, and clamped by the threaded screw, which has a rotary head. The actual gripping power brought to bear on the rod depends on the ratio of the distance between the axis of the loading device and the axis of the rod to the distance between the axis of the loading device and the support of the clamping component of the pressure disc. In order to achieve the most effective possible grip on the rod for a given loading device, according to the law of leverage, the aforementioned ratio must be as small as possible. The consequence is that the gripping components are inevitably larger in size. These gripping connections, used particularly for external fixation in osteosynthesis, are used chiefly for setting small parts of the body, a use in which the gripping components must not be too large. In practice, it has been found that for the reasons indicated the gripping power achieved with clamps of the type described is not firm enough, and thus a secure bracing between the construction components or the setting device as a whole is not achieved. In addition, it often happens that the gripping power weakens after a certain time and thus fixation no longer exists at all.

Another gripping device, described in WO-A1 88/01152, provides for gripping discs similar to that described above. A pair of these gripping discs position a screw or similar device in semi-circular recesses and grip it by means of a screw positioned axially to them. To hold two construction components, two pairs of such gripping discs are provided for one loading screw. Theoretically, this gripping device has the same disadvantages as the device described above, because the gripping power actually exerted on a rod similarly assumes an unfavorable ratio of distance between the axis of the bracing screw and the support of the gripping discs. This is not altered by the construction of the gripping discs on the support with toothed gearing provided on each side. In this known, open system, the oblique plane present is used not to improve the grip but merely to improve the centering between the connection and the gripping component.

SUMMARY OF THE INVENTION

To eliminate the disadvantages of the device described above, the present invention provides a clamp which, by a simple manual operation, creates a strong, long-lasting, and more or less continuous gripping force connecting two construction components.

Specifically, the invention comprises a clamp for connecting two construction components comprising a connection component, a clamping component, clamping means associated with said clamping component, means in said connection component and in said clamping component for receiving a construction component, and loading means for applying a loading force along a force axis, said clamping component resting on said connection component and being positioned to be pressed by a moment created by said loading force against the connection component, thereby to develop a frictional force between the clamping and connection components which acts to reduce the force applied to the construction component.

A clamp according to the invention has the particular advantage of facilitating a significantly greater resulting gripping power with the same size and the same applied loading force as in the state-of-the-art technology. In addition, the design of the clamp is very flexible, so that vibrations and similar events will not dissolve the connection, enabling the long-term clamping effect to continue to exist.

To achieve a maximum gripping power exerted on the construction component, the ratio of the distance between the axis of the construction component and the axis of the loading force to the distance between the construction component axis and the line of action of the support force should be less than 1.0, and preferably should be between 0.6 and 0.1.

The loading surfaces of the connection and construction components, or the support surfaces of the gripping and connection components, are as smooth as possible, for their mutual, more or less frictionless, support.

The connection component can be cylindrical or rectangular, or have any other shape, and on each end it has a threaded screw, both screws having the same axis, with a cup-shaped clamping component being positioned on the screws, which cup-shaped component exerts a compressive force on the construction element gripped in between, and, with its support surface parallel to the loading axis, engages the support surface of the connection component. Depending on the individual case, these corresponding support surfaces are cylindrical or flat.

BRIEF DESCRIPTION OF THE DRAWINGS

The invention will be further described with reference to the accompanying drawings, in which.

DETAILED DESCRIPTION OF EMBODIMENTS OF THE INVENTION

Figure 1:
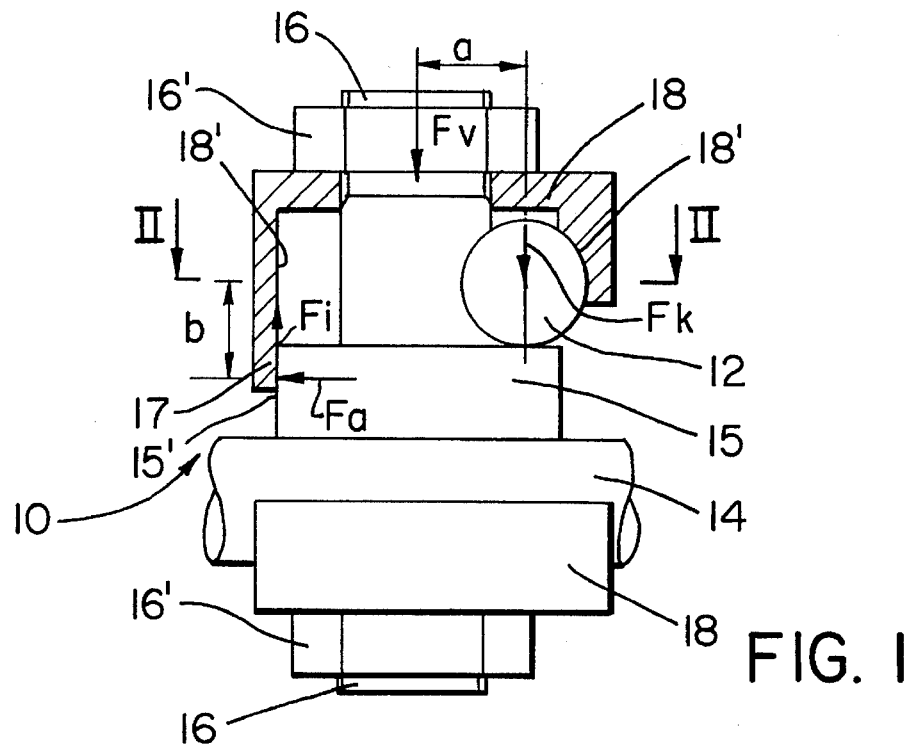
FIG. 1 is a view in side elevation and partly in vertical section of a clamp connection according to the invention.

FIG. 1 shows a clamp 10 as a component of an osteosynthetic fixation device not illustrated in detail, which fixation device comprises two construction components 12 and 14 connected to one another through clamp 10. Said construction components may consist, for example, of a connection rod and a Schanz screw, which screw may be driven into, for example, a portion of a broken finger bone. A second clamp can then appropriately connect another screw in the other bone part with the connection rod.

The clamp 10 comprises a connection component 15 and on both of its ends loading devices each comprising threads on a central rod 16 which receive nuts 16'. Two clamp components 18 are provided. These are cup-like elements having asymmetrical holes and a side wall which on one side is longer than on the other side On the shorter side, as at 18', an arcuate recess is provided to receive construction component 12. As shown in FIG. 1, central rod 16 is placed through the asymmetrical hole in clamp component 18 and component 18 slides over connection element 15 so that its longer side wall engages the side of element 15.

As shown in FIG. 1, the lower clamp component 18, which is the same as the upper component shown in cross-section, is rotated 90° and receives a second construction component 14 in the same way the construction component 12 is received in the upper part of the device.

According to the invention, the clamp component 18 engages the connection component 15, parallel to the direction of loading force Fv, and through the moment created by force Fv is pressed on connection element 15 with a bearing force Fa acting perpendicular to loading force Fv, which bearing force Fa creates a frictional force Fr between the clamp and connection component, which is the only force reducing the loading effect of the force Fv acting on the relevant construction component 12. In contrast to the direct bearing characteristic of conventional devices, in this invention the friction Fr is on the one hand smaller by the factor of the friction coefficient; on the other hand, the ratio of the distance between the axis of construction component 12 and the axis of loading force Fv to the distance b between the axis of construction component 12 and the line of action of bearing force Fa is less than 1.0, and is preferably between 0.6 and 0.1. This can be achieved without any need to enlarge the diameter of the clamp component 18 and hence the clamp 10 as a whole.

Figure 2:
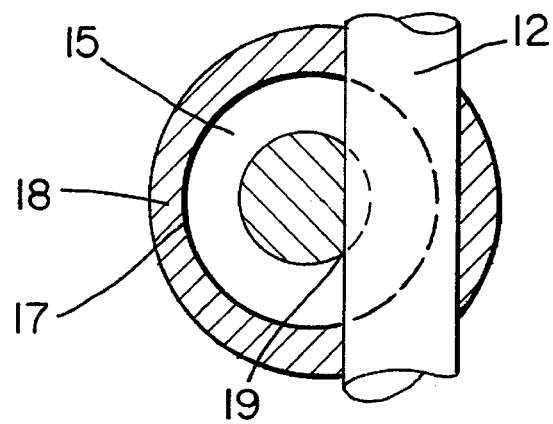
FIG. 2 is a plan view, partly in horizontal section at cross-section II—II of FIG. 1.

As shown in FIG. 2, the cylindrical clamp component 18 encompasses construction component 12 and connection component 15. Threaded screw 16 in the center of connection component 15 has a pressure channel 19 into which the construction component 12 fits. This leads to a reduction in the size of the clamp. The clamp and connection component could also be rectangular, or have any other shape.

Figure 3:
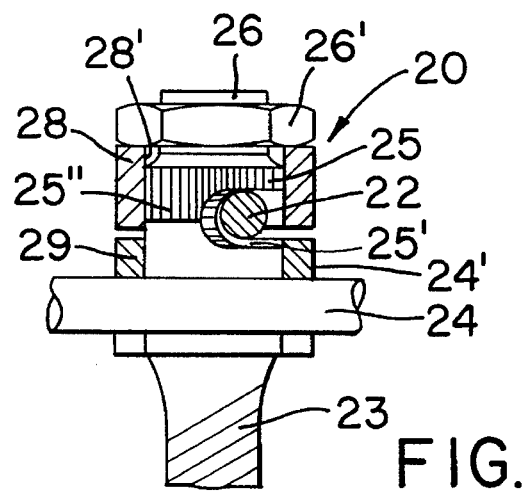
FIG. 3 is a view in elevation and partly in vertical section of another embodiment of the invention with a pedicle screw.

FIG. 3 shows a clamp connection 20, which comprises a cylindrical connection component 25 formed at the head of a pedicle screw 23, and two annular clamp components 28, 29 positioned to slide axially on the pedicle screw 23. Connection component 25 has a threaded end 26 and a nut 26' is screwed onto this threaded end 26, which nut 26' comes into contact with top clamp component 28. When nut 26' is turned down, clamp component 28 presses on a construction component 22, shown as a transverse rod, which construction component 22 in turn presses on the second clamp component 29 and presses it on another construction component 24, which, like the construction component 22, is supported by connection component 25, being positioned in a groove-shaped recess 24', in connection component 25. The two recesses 24', 25' are one above the other and are offset in relation to each other at an angle of 90°, and at least one of them is designed in such manner that the transverse rod positioned in it can be adjusted by a few degrees, e.g. 40°, to the connection component 25. The pedicle screw 23, positioned coaxially to the connection component 25, is thereupon screwed into a bone or similar substance, while the construction component 22 and the construction component 24 are connected as part of a fixation device with additional clamp connections. Surfaces 28', 25", of clamp component 28 and connection component 25 are rotationally symmetrical, and in the contact area they preferably have toothing, so that they can be slid, but not turned, against each other practically without friction along the loading axis. The position of construction component 22 in relation to element 26, is maintained by a non-rotatable design of the interior surface of clamp component 28 and external surface of element 26, preferably by longitudinal toothing or by a non-cylindrical geometry of element 26 and clamp component 28, preferably by a polygonal (e.g. hexagonal) shape.

Figure 4:
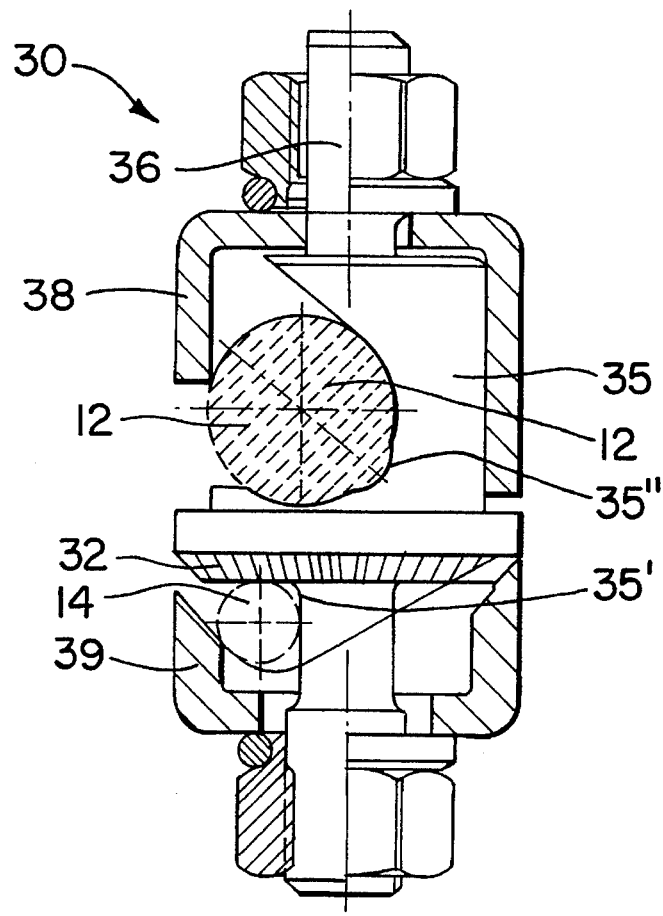
FIG. 4 is a view in vertical section of another variant of a clamp according to the invention.

A clamp 30 according to FIG. 4 has two clamp components 38, 39 and an essentially cylindrical connection component 35 with threaded extensions 36, at either end. Components 38, 39 are coaxial with the connection component 35. Connection component 35 has recesses 35', 35", which serve to receive construction components 12, 14. Lateral recess 35" is designed in such manner that through its roughly semi-circular design it creates a three-point bearing when a construction component 12 is seated in it. Advantageously, construction component 12 is tubular, so that for purposes of increasing the clamping effect, it undergoes a certain deformation, in adapting to recess 35". The other construction component 14 is pressed by clamp component 39, which forms a longitudinal groove, into the practically rectangular recess 35' of the connection component. The clamping component 39, and connection component 35, are positioned facing each other and in such manner that they cannot turn against each other by means of cylindrical toothed element 32; in the direction of loading, in contrast, they are positioned to be in contact with each other as frictionlessly as possible.

Figure 5:
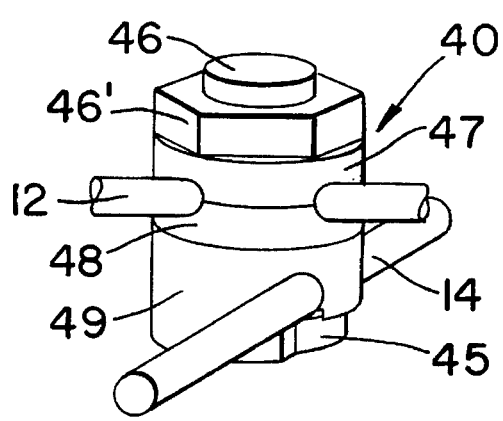
FIG. 5 and FIG. 6 are perspective views of a further variant of a clamp according to the invention.

FIG. 5 shows yet another clamp connection 40 for joining in particular a Schanz screw 12 with a transverse rod 14 in an external fixation device. In contrast to the clamp connection illustrated in FIG. 1, only one loading means 46, 46' is provided for the two rods to be clamped. A nut 46' comes into contact with a top clamp component 47, which has a longitudinal recess for Schanz screw 12. Screw 12 in turn rests on a spacing collar 48 that rests on bottom clamp component 49. Spacing collar 48 exerts a loading force on clamp component 49, which clamps transverse rod 14 to a connection component 45. The two clamp components 47 and 49 rest on connection component 45, unitary with component 46 opposite the rods, parallel to the direction of compression, so that the aforementioned friction is created as a reduced counter-force in the clamping operation.

Figure 6:
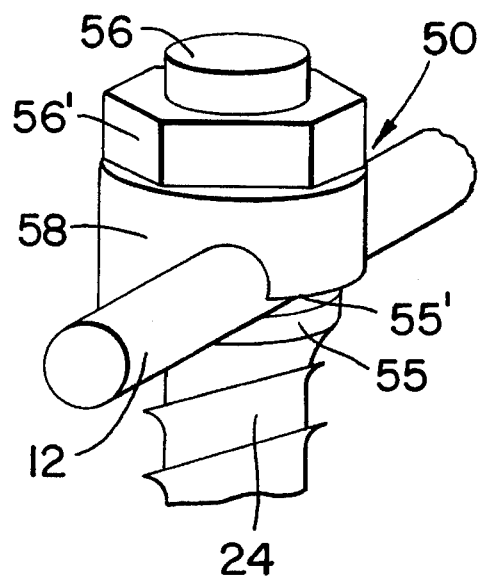

Clamp 50 according to FIG. 6 differs from the clamp connection according to FIG. 3 only by the fact that connection component 55 has a single transverse recess 55' for a construction component 12. Otherwise, here again, a loading force can be exerted, via clamp component 58, on construction component 12, by the screw and nut 56, 56', and said construction component 12 is clamped. Moreover, the cylindrical connection component 55 has a coaxial pedicle screw 24.

Figure 7A:
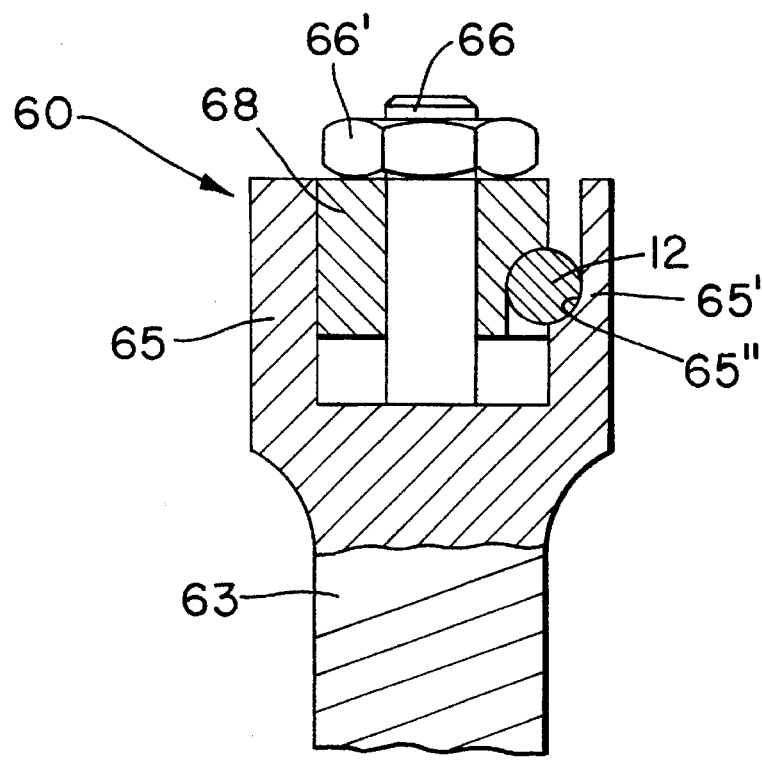
FIG. 7a and 7b are vertical sections through another variant of a clamp according to the invention.
Figure 7B:
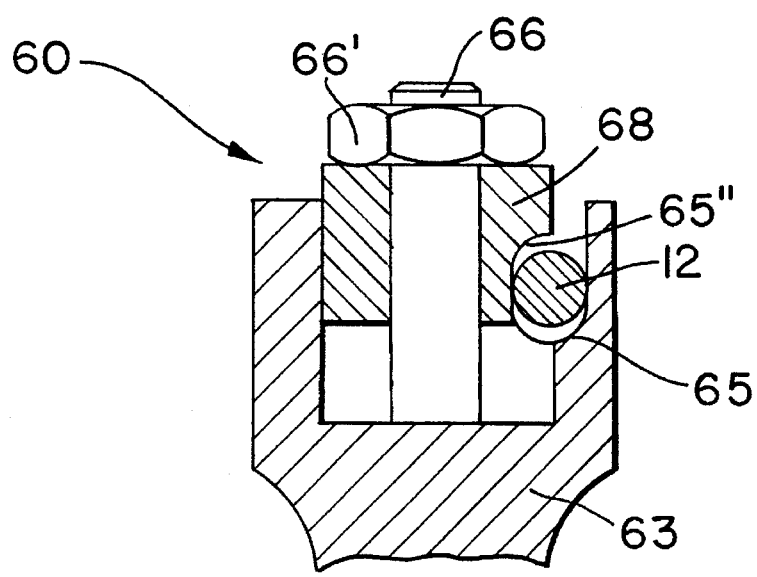

The clamp connection 60 according to FIG. 7a and 7b has an essentially cylindrical connection component 65 on a pedicle screw 63 with a cylindrical recess 65', in which a coaxial threaded screw 66 is positioned. On the screw 66 an external cylindrical clamping component 68 is positioned. It fits into the recess 65' and can be slid therein by a nut 66'. A construction component 12 that is lateral and transverse to the axis of the threaded screw 66, and which is positioned in an off-center slot of the connection component 65, is clamped by the loading force created by screw and nut 66, 66' on clamping component 68 to an internal bearing surface 65" of connection component 65. Opposite it, clamp component 68 according to the invention bears, parallel to the loading direction, on connection component 65, whereby the desired most effective possible gripping power on construction component 12 is achieved.

In this embodiment, recess 65' and internal bearing surface 65" can be designed in two different ways. In FIG. 7a, components 65' and 65" correspond to the shape of construction component 12; in FIG. 7b, they are designed in such manner that in combination with clamping component 68 they create a three-point bearing.

Needless to say, the invention can also be embodied in other variants. It should be noted, in this connection, that theoretically instead of a screw/nut connection, another known principle could be used to develop a loading force.

It is claimed:

1. A clamp for securing a support rod comprising a clamping component having a cylindrical through hole and a socket adapted to receive a support rod, a connecting component having a base section and a cylindrical leg integrally formed with said base section and having a central axis extending from said base section into said through hole, and loading means mounted in said leg, said connecting component and said clamping component having curved surfaces in contact with each other, said curved surfaces being cylindrical about a central axis coinciding with the central axis of said leg, said loading means being positioned to bear against said clamping component to cause said clamping component to press a rod inserted in the socket of said clamping component against the base section of said connecting component and to press the curved surface of said clamping component against the curved surface of said connecting component.

2. A clamp for securing a rod comprising a clamping component having a through hole and a socket adapted to receive a rod, a connecting component having a cylindrical base section with a central axis, and a leg extending from said base section along said central axis through the through hole of said clamping component, said connecting component having a surface in lateral contact with a surface of said clamping component, in combination with loading means mounted in said leg and positioned to bear against said clamping component thereby to cause said clamping component to press a rod inserted in said socket against the base section of said contacting component and to press said laterally connecting surfaces of said clamping and connecting components against one another.

3. The clamp claimed in claim 1 wherein the clamping component is cup shaped.

4. The clamp claimed in claim 3 wherein the clamping component has an upper surface and a skirt having a long section and a short section.

5. The clamp claimed in claim 4 wherein the long section of said skirt has a surface in contact with said connecting component.

6. The clamp claimed in claim 1 wherein the connecting component has a lateral socket for receiving a rod.

7. The clamp claimed in claim 6 wherein the socket of the connecting component is shaped to permit swinging movement of a rod seated therein.

8. The clamp claimed in claim 1 wherein the connecting component base section has a roughened surface in lateral contact with a surface of said clamping component.

9. The clamp claimed in claim 1 wherein the clamping component has a roughened inner surface in lateral contact with a surface of said connecting component.

10. The clamp claimed in claim 7 wherein the connecting component base section has a roughened surface in lateral contact with a surface of said clamping component.

11. The clamp claimed in claim 1 wherein the connecting component is cup shaped and has a peripheral wall.

12. The clamp claimed in claim 11 wherein the peripheral wall has a recess for receiving a rod.

13. The clamp claimed in claim 11 wherein the peripheral wall has an inner surface which is in lateral contact with a surface of the clamping component.

* * * * *